(12) United States Patent
Lovegrove et al.

(10) Patent No.: US 9,103,815 B2
(45) Date of Patent: Aug. 11, 2015

(54) APPARATUS FOR TESTING ELECTRICAL ACTIVITY FROM A BIOLOGICAL TISSUE SAMPLE

(75) Inventors: David Lovegrove, Christchurch (NZ); Douglas Steven Kerr, Dunedin (NZ); David James Haughey, Christchurch (NZ); Michael Paul Ronayne, Manukau (NZ); Darryl John Best, Christchurch (NZ)

(73) Assignee: Kerr Scientific Instruments Limited, Christchurch (NZ)

( * ) Notice: Subject to any disclaimer, the term of this patent is extended or adjusted under 35 U.S.C. 154(b) by 857 days.

(21) Appl. No.: 13/129,059

(22) PCT Filed: Nov. 12, 2009

(86) PCT No.: PCT/NZ2009/000250
§ 371 (c)(1),
(2), (4) Date: May 12, 2011

(87) PCT Pub. No.: WO2010/056136
PCT Pub. Date: May 20, 2010

(65) Prior Publication Data
US 2011/0223651 A1 Sep. 15, 2011

Related U.S. Application Data

(60) Provisional application No. 61/114,042, filed on Nov. 12, 2008.

(51) Int. Cl.
*C12M 1/34* (2006.01)
*B01L 9/00* (2006.01)
(Continued)

(52) U.S. Cl.
CPC ................................ *G01N 33/4833* (2013.01)

(58) Field of Classification Search
CPC .. G01N 33/4833; H01L 23/46; H01L 23/473; B01L 9/00; F28F 7/00
USPC .................. 435/287.1; 422/561, 560; 165/185
See application file for complete search history.

(56) References Cited

U.S. PATENT DOCUMENTS 6,048,722 A * 4/2000 Farb et al. .................. 435/287.1
6,773,678 B2 8/2004 Cummings et al.
(Continued)

FOREIGN PATENT DOCUMENTS

WO 01/71312 A2 9/2001

OTHER PUBLICATIONS

PowerLab System, "Kerr Brain Slice System Owner's Guide," PowerLab AdInstruments, (2008).
(Continued)

*Primary Examiner* — William H Beisner
*Assistant Examiner* — Danielle Henkel
(74) *Attorney, Agent, or Firm* — Nelson Mullins Riley & Scarborough LLP; Jane E. Remillard, Esq.; Cynthia L. Kanik (57) ABSTRACT

An apparatus (100) for testing electrical activity from a biological tissue sample comprises a body (1) provided with a well (4), stimulating means (8) for stimulating a sample located in the well (4), and detecting means (9) for detecting electrical activity in the sample. In one embodiment the apparatus has a fluid inlet means (10) and a fluid outlet means (16) in fluid communication with the well (4). The inlet means (10) comprises an electrically conductive conduit (11A) which is in fluid contact with a fluid flowing, in use, though the outlet means (16). In some embodiments the apparatus is provided with an electrically conductive member (19) which is in electrical contact with a fluid contained, in use, in at least one of the well (4), inlet means (10) and outlet means (16). The stimulating means (8) and detecting means (9) are engaged with the body (1) by a gripping means (32) which comprises an electrically conductive gripping member (36). Related methods and apparatus are also disclosed.

10 Claims, 9 Drawing Sheets

(51) Int. Cl.
*F28F 7/00* (2006.01)
*G01N 33/483* (2006.01)

(56) References Cited

U.S. PATENT DOCUMENTS

2005/0131463 A1* 6/2005 Fedorov et al. .................. 607/2
2007/0238112 A1 10/2007 Sohn et al.

OTHER PUBLICATIONS

International Search Report for Application No. PCT/NZ2009/000250, dated Mar. 16, 2010.
International Preliminary Report on Patentability for Application No. PCT/NZ2009/000250, dated May 17, 2011.

\* cited by examiner

APPARATUS FOR TESTING ELECTRICAL ACTIVITY FROM A BIOLOGICAL TISSUE SAMPLE

RELATED APPLICATIONS

This application is a 35 U.S.C. §371 national stage filing of PCT Application No. PCT/NZ2009/000250, filed on Nov. 12, 2009, which claims priority to U.S. Provisional Patent Application No. 61/114,042, filed on Nov. 12, 2008. The entire contents of the aforementioned applications are hereby incorporated by reference.

The present invention relates to equipment for testing electrical activity from biological tissue, and in particular, but not exclusively, to a portable system which is easily disassembled.

BACKGROUND TO THE INVENTION

The present invention relates to laboratory equipment, commonly referred to as "tissue recording chambers" or "brain slice chambers" which allow the user to record and assess the effects of drugs and toxins on living, electrically excitable tissues.

Apparatus of this type are often used to analyse the effects of drugs and/or neurotoxins on brain tissue from rats. However, recording techniques have been recently adapted to include cardiac tissue. Other excitable tissues of potential interest are skeletal muscle and retina.

In an example of a tissue recording system of the prior art, fluids are directed into a chamber through a small diameter stainless steel tube which projects into a tissue recording chamber, also known as a slice bath. The fluids contain oxygen, salts and essential nutrients for the tissue, as well the toxins or drugs which are the object of the study.

The subject tissue slice is held in position between two nets. Fluids superfuse the tissue and then flow into a reservoir or moat or which directs the fluids out again through a separate channel and into a suction port. The fluids are drawn out of the suction port by a disposable small gauge needle fitted to an adjustable post which allows the user to regulate the level of the fluid in the suction port, and therefore in the recording chamber. The fluids are finally drawn away from the tissue recording system via a length of flexible tubing which extends between the needle and a vacuum source.

An electrical stimulus is applied to the tissue slice via an electrode connected to a micromanipulator. The signal produced by the tissue sample is recorded by a second electrode held in a second micromanipulator. An amplifier is provided in the base of the micromanipulator to amplify the signal before it is recorded by a data recording system.

The prior art apparatus described above has a number of inherent disadvantages.

Electrical grounding and communication of the recording chamber 'bath potential' to the amplifier is achieved by a small spring loaded pin which is pressed into the underside of the recording chamber to make contact with a stainless steel fluid input tube. The pin also makes contact with the upper surface of an annular grounding ring pressed into the recording chamber platform. The upper surface of the grounding ring is also in contact with a spring loaded pin which is in direct contact with an amplifier housed in the base of the micromanipulator.

This system of grounding works reasonably well in terms of grounding noise entering the system via the input tube, but may fail to adequately ground noise entering the system through the vacuum line and suction port. In addition, the spring loaded pins may be physically weak and prone to failure following several years of use.

Recording and stimulating electrodes are positioned over the tissue slice using modular attachable micromanipulators which are designed to hold adjustable tubular steel electrode guides. The guides hold fixed electrodes. The electrode pin sockets are permanently affixed in plastic end caps and the user then manually connects the electrodes for use on a daily basis.

The tubular steel probe guides are gripped in the 'arms' of the micromanipulators and can be slid up or down as needed to allow the micromanipulator arm to be swung aside for placement of fresh slices in the bath. However, the extremely delicate electrodes themselves are in danger of damage, and the probe guides can not be removed for storage without first removing the individual electrodes.

The tissue sample is held in position in the bath between two net rings. The two rings fit together, one within the other, and are referred to as the top net and the bottom net. Together they serve to sandwich and stabilize tissue slices for vibration-free recording.

The nets are relative fragile. If the nets are torn during use, which is reasonably common, then the user has to sand away and manually replace the netting material. With repeated use the net rings tended to lose their original fit, becoming too tight, and requiring sanding or honing, or too loose, requiring the fabrication of spacers or shims to prevent slippage. Because they often fit very snugly in the bath and to one another, and because they are small and difficult to grip, a special tool is required to remove the net rings.

OBJECT OF THE INVENTION

It is an object of the invention to provide an apparatus for testing electrical activity from a biological tissue sample which will overcome or ameliorate problems with such apparatus at present, or at least one which will provide the public with a useful choice.

It is an alternative object of the invention to provide a mounting means for an electrode which will overcome or ameliorate problems with such apparatus at present, or at least one which will provide the public with a useful choice.

It is a further alternative object of the invention to provide a net assembly adapted to hold a biological tissue sample in position in an apparatus for testing electrical activity from sample, or at least one which will provide the public with a useful choice.

Other objects of the present invention may become apparent from the following description, which is given by way of example only.

SUMMARY OF THE INVENTION

According to one aspect of the present invention there is provided an apparatus for testing electrical activity from a biological tissue sample, the apparatus comprising a body provided with a well, the apparatus further comprising stimulating means for stimulating a biological tissue sample which is located, in use, in the well, and detecting means for detecting electrical activity in the tissue sample, the body provided with a fluid inlet means in fluid communication with the well and outlet means comprising an upwardly open outlet port in fluid communication with the well, and adjustable fluid level regulation means adapted to draw fluid, in use, from the upwardly open outlet port at a required level, the outlet means comprising an outlet aperture which is substantially fixed in position relative to the body.

Preferably the outlet aperture is provided in the body of the apparatus.

Preferably the fluid level regulation means comprises an elongate member with a suction inlet means provided at or adjacent a first end, and a second, distal end of the elongate member adapted to sealingly and slidingly engage a mounting aperture in the body, wherein the level of the suction inlet means relative to the upwardly open port can be adjusted by sliding the elongate member up or down in the mounting aperture.

Preferably the fluid regulation means is provided with a conduit between the inlet means and the distal end of elongate member.

Preferably the mounting aperture is in fluid communication with the outlet aperture.

Preferably the suction inlet means comprises means for mounting a disposable needle.

According to a second aspect of the present invention there is provided an apparatus for testing electrical activity from a biological tissue sample, the apparatus comprising a body provided with a well, the apparatus further comprising stimulating means for stimulating a biological tissue sample which is located, in use, in the well, and detecting means for detecting electrical activity in the tissue sample, the apparatus further comprising a fluid inlet means in fluid communication with the well and a fluid outlet means in fluid communication with the well, wherein the inlet means comprises an electrically conductive conduit which is in fluid contact with a fluid flowing, in use, though the outlet means.

Preferably the outlet means comprises an outlet passage provided in the body, and the electrically conductive conduit means extends into the outlet passage.

Preferably the electrically conductive conduit has an electrical resistivity of less than $1\times10^{-6}$ $\Omega$m at room temperature.

Preferably the electrically conductive conduit has a thermal conductivity of at least 10 W/m K at room temperature.

Preferably the outlet means comprises a passage adapted to receive a heating element such that the heating element is in thermal contact with fluid flowing though the outlet conduit upstream of the electrically conductive conduit, to thereby transfer heat to the fluid in the inlet means through the electrically conductive conduit.

According to a third aspect of the present invention there is provided a method of heating a fluid entering an apparatus for testing electrical activity from a biological tissue sample, the apparatus comprising a fluid inlet means comprising a thermally conductive inlet conduit and a fluid outlet means which has a portion in fluid contact with the thermally conductive inlet conduit, the method comprising heating a fluid flowing through the outlet means upstream of the thermally conductive inlet conduit and transferring heat from the fluid in the outlet means to the fluid in the inlet conduit though the thermally conductive inlet conduit.

According to a fourth aspect of the present invention there is provided an apparatus for testing electrical activity from a biological tissue sample, the apparatus comprising a body provided with a well, stimulating means for stimulating a biological tissue sample located, in use, in the well, and detecting means for detecting electrical activity in the tissue sample, a fluid inlet means in fluid communication with the well and a fluid outlet means in fluid communication with the well, the apparatus further comprising an electrically conductive member in electrical contact with a fluid contained, in use, in at least one of the well, inlet means and outlet means, wherein at least one of the stimulating means and detecting means is engaged with the body by a gripping means which comprises an electrically conductive gripping member which engages the electrically conductive member, and the electrically conductive gripping member is electrically connectable to a data recording system which, in use, records the electrical activity from the sample.

Preferably the electrically conductive member is in electrical contact with a fluid contained, in use, in both the inlet means and the outlet means.

Preferably, the electrically conductive member comprises an annular ring.

Preferably the annular ring is set into the body.

Preferably, the electrically conductive gripping member exerts a force on an inner surface of the annular ring in a radially outward direction.

According to a fifth aspect of the present invention there is provided a mounting means for an electrode, the mounting means comprising a base and an electrode engaging means connected to the base, the electrode engaging means comprising a sheath provided with releasable electrode gripping means at a first end for releasably gripping the electrode, wherein the sheath is shaped and dimensioned to allow the electrode to be retracted within the sheath to a stored position.

Preferably the sheath is a hollow tube.

Preferably the releasable gripping means comprises a chuck.

Preferably the chuck is a collet chuck.

Preferably the collet chuck is integral with the sheath.

Preferably the sheath is provided with releasable wire gripping means at the distal end to the releasable electrode gripping means.

According to a sixth aspect of the present invention there is provided a net assembly adapted to hold a biological tissue sample in position in an apparatus for testing electrical activity from sample, the net assembly comprising a first net means having a first substantially annular frame and a netting material extending across one end of the first cylindrical frame, the first net means nestably engageable with a second net means having a second substantially annular frame and a netting material extending across one end of the second annular frame, wherein the first net means comprises a plurality of tab formations extending radially outward from a distal end of the first frame to the netting material.

Preferably an inner surface of the first annular frame is substantially frusto-conical.

Preferably, the first net means comprises a plurality of tab formations substantially evenly spaced around the first frame.

Preferably the second net means comprises at least one tab formation extending radially outward from the second frame at a distal end to the netting material.

Preferably the second net means comprises a plurality of tab formations substantially evenly spaced around the second frame, wherein the second net means is provided with a different number of tab formations to the first net means.

According to a further aspect of the present invention there is provided an apparatus for testing electrical activity from a biological tissue sample substantially as herein described with reference to the accompanying drawings.

According to a still further aspect of the present invention there is provided a net assembly substantially as herein described with reference to FIGS. 6 and 7.

The invention may also be said broadly to consist in the parts, elements and features referred to or indicated in the specification of the application, individually or collectively, in any or all combinations of two or more of said parts, elements or features, and where specific integers are mentioned herein which have known equivalents in the art to which the invention relates, such known equivalents are deemed to be incorporated herein as if individually set forth.

Further aspects of the invention, which should be considered in all its novel aspects, will become apparent from the following description given by way of example of possible embodiments of the invention.

BEST MODES FOR PERFORMING THE INVENTION

Figure 1:
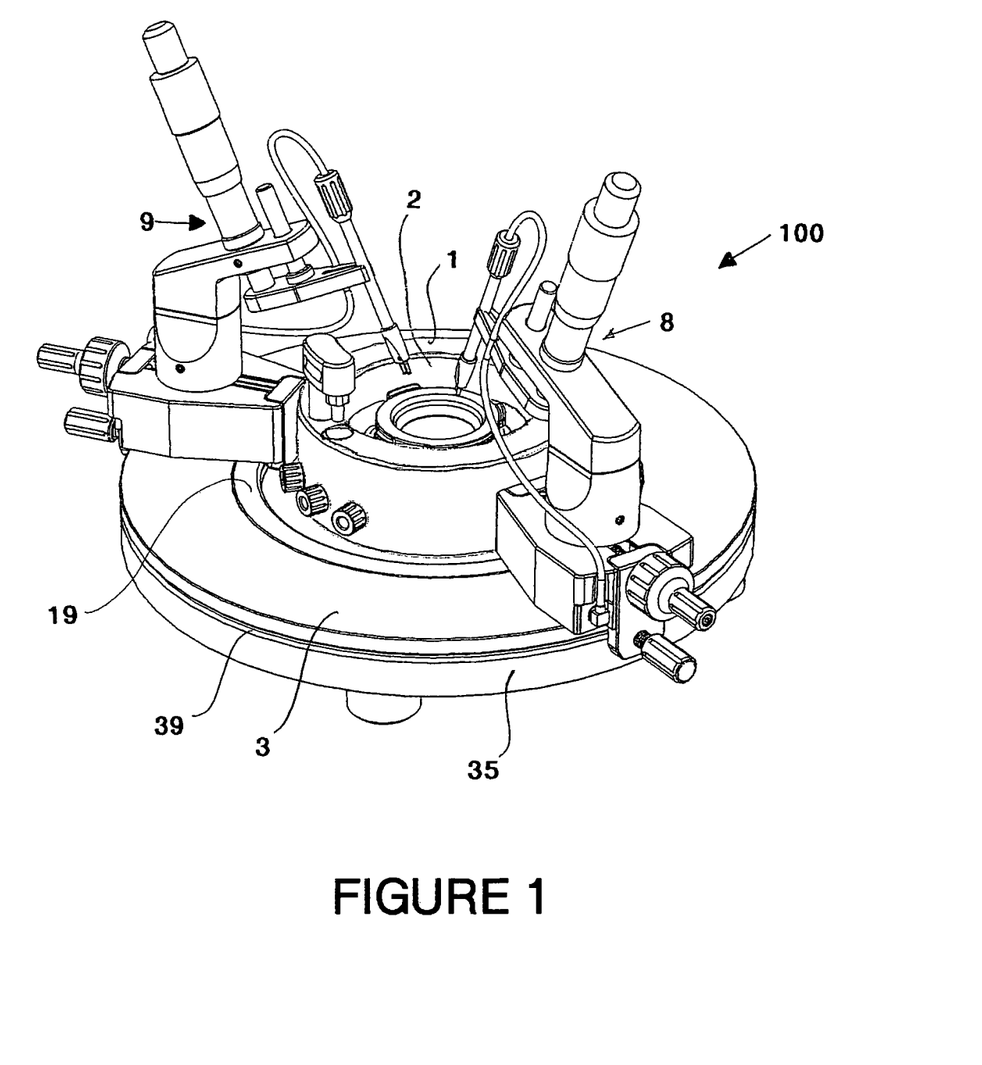
FIG. 1: Is a perspective view of the apparatus of the present invention.
Figure 2:
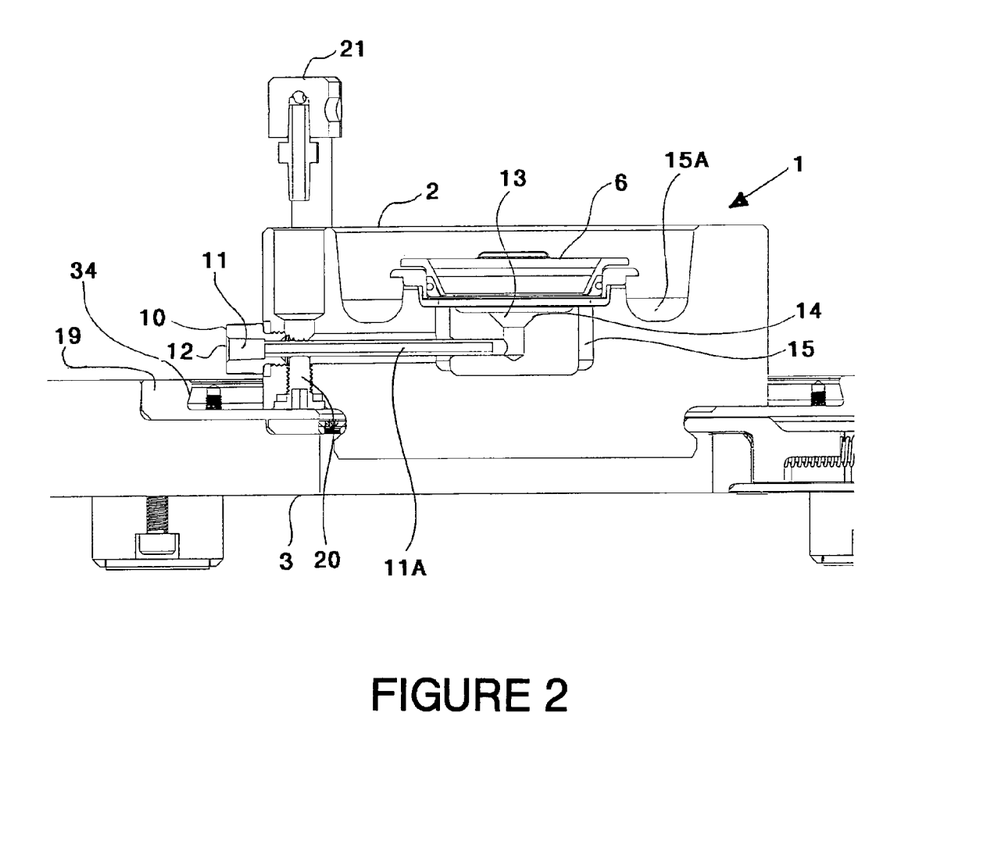
FIG. 2: Is an enlarged cross-section side view through the centre of the apparatus of FIG. 1, with the stimulating and detecting means removed for clarity.
Figure 2A:
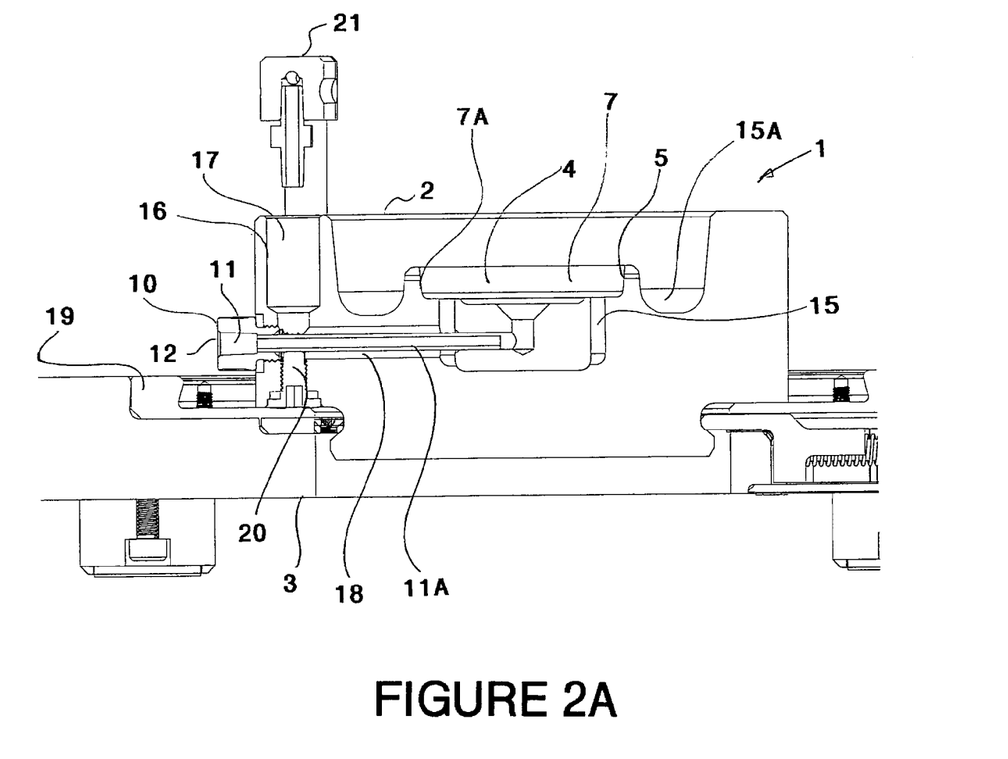
FIG. 2A: Is the cross-section of FIG. 2, with the net assembly removed for clarity.

Referring first to FIGS. 1, 2 and 2A, the apparatus 100 of the present invention comprises a body 1 having a chamber assembly 2 which is connected to or integral with a base 3. The base 3 is preferably substantially disc shaped. A well 4 is formed within the chamber assembly 2, as is best seen in FIG. 2A.

The well 4 comprises a cradle formation 5 for holding a net assembly 6 within which the tissue sample (not shown) is held. The cradle formation 5 is preferably provided with a substantially cylindrical recess 7. The inner walls 7A of the recess 7 preferably taper slightly inwardly.

Stimulating means 8, for stimulating the tissue sample, and detecting means 9, for detecting electrical activity in the tissue sample, are mounted to the body 1.

A fluid inlet means 10 is provided though the body 1 to allow a perfusion fluid to flow into the well 4. The inlet means 10 comprises a conduit 11 provided with an inlet aperture 12 outside the well 4 and an outlet 13 beneath the cradle. The outlet 13 is formed into a diffuser portion 14 which expands outwardly in the direction of the fluid flow. The diffuser portion 14 terminates directly below the cradle 5 and directs the fluid evenly through the net assembly 6 and over the tissue sample.

The inlet conduit 11 comprises a portion formed from an electrically conductive material such as a stainless steel tube 11A. The tube 11A is preferably both electrically conductive and thermally conductive, as is described further below. The electrically conductive material preferably has an electrical resistivity of less than $1 \times 10^{-6}$ $\Omega$m and a thermal conductivity of at least 10 W/mK.

In use, the perfusion fluid flows from a source (not shown) through the inlet conduit 11. The fluid flows from the outlet 13 of the inlet conduit, through the net assembly 6 and over the tissue sample, and into an inner moat portion 15 of the well 4.

An outlet means 16 comprises an upwardly open port 17 provided in the body 1. The port 17 is in fluid communication with the well 4, for example by means of an outlet passage 18 provided in the body 1 between the upwardly open port 17 and the well 4. In a preferred embodiment the stainless steel tube 11A extends through a portion of the outlet passage 18, so that the stainless steel tube 11A is fluid contact with the fluid flowing though the outlet passage 18.

Because the tube 11A is electrically conductive, it conducts any electrical charge from both the fluid stream flowing into the apparatus 100 through the inlet means 10, and the fluid stream flowing out of the apparatus though the outlet means 16.

The tube 11A is in electrical contact with a common earth means. In a preferred embodiment the common earth means is an electrically conductive annular member 19 which is electrically connected to the steel tube 11A by means of a grounding screw 20. The grounding screw 20 preferably extends into the outlet passage 18 so as to be in contact with the fluid in both the outlet passage 18 and the inlet conduit 11A.

Figure 3:
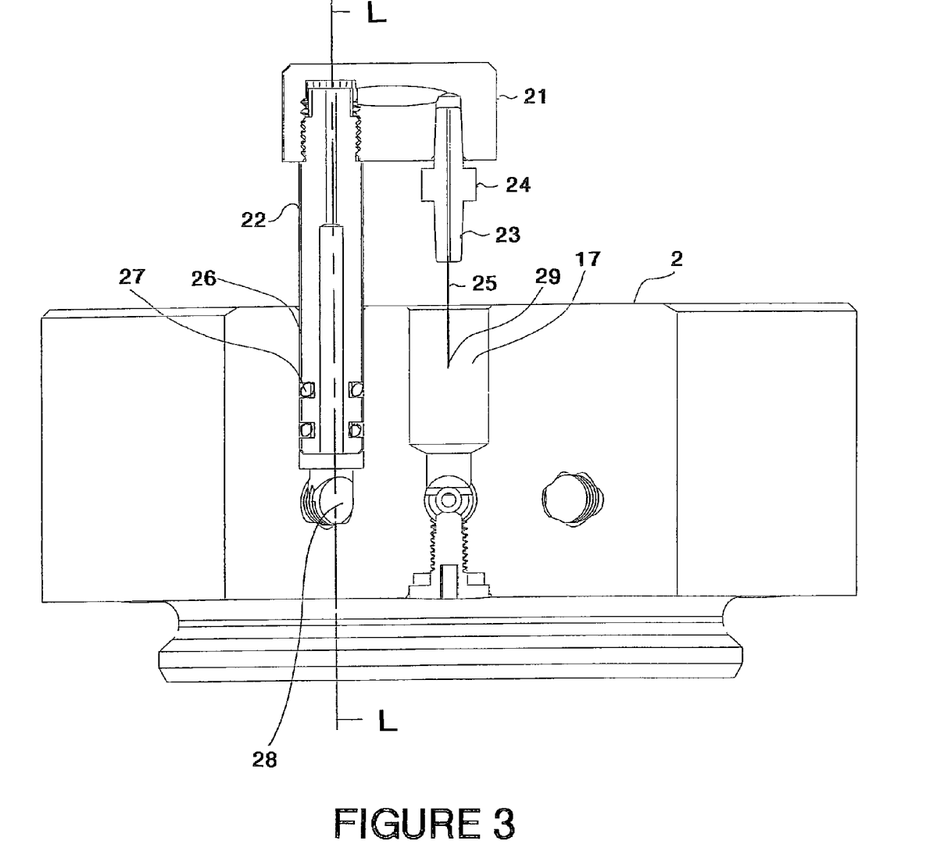
FIG. 3: Shows a front view of the well assembly of the apparatus of FIG. 1 in partial cross-section through the adjustable fluid level regulating means, and with a needle engaged with the fluid level regulation means.
Figure 4:
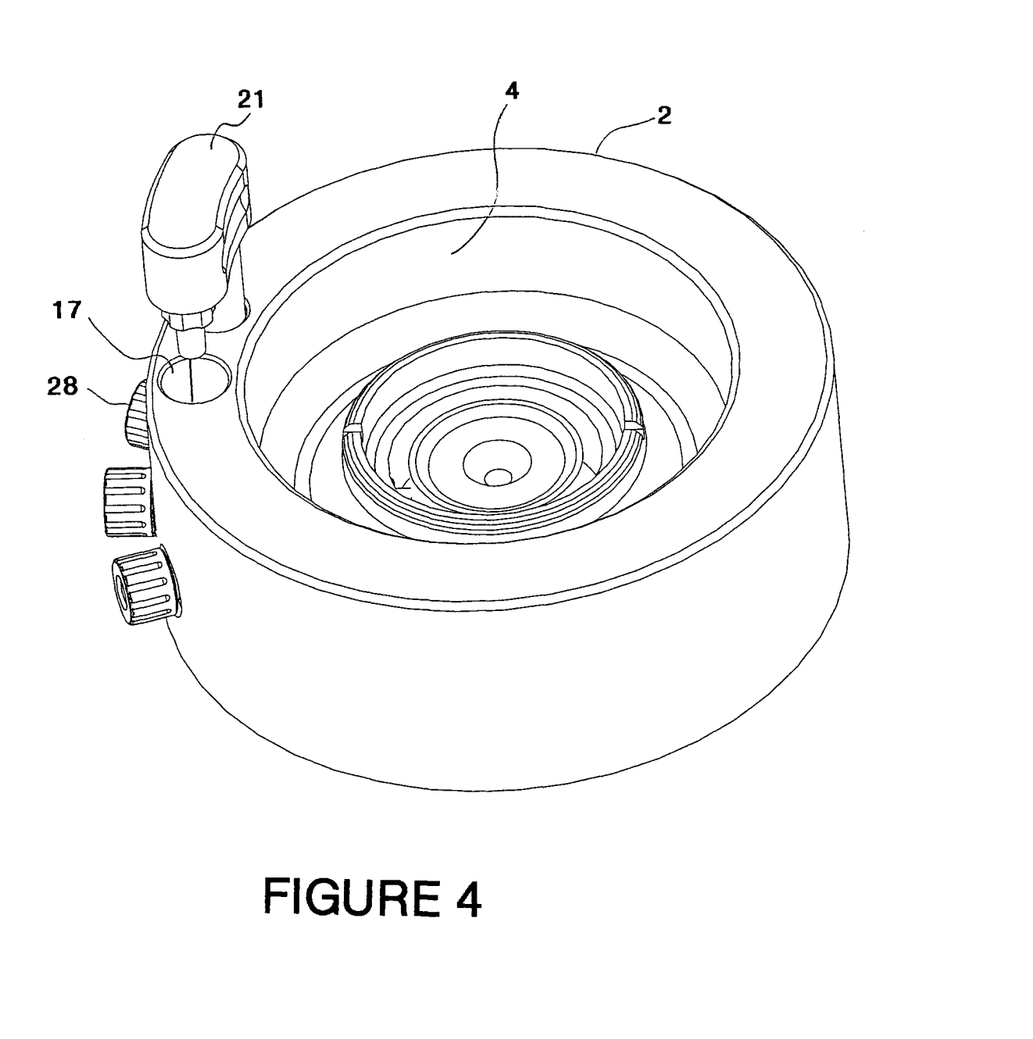
FIG. 4: Shows a perspective view of the well assembly and fluid level regulating means of the apparatus of FIG. 1, with a needle engaged with the fluid level regulation means.

Referring next to FIGS. 2 to 4, and in particular FIG. 3, an adjustable fluid level regulation means 21 is provided to regulate the level of the fluid in the well 4. The fluid regulation means 21 comprises an elongate member 22 connected to a suction inlet means 23. In a preferred embodiment the suction inlet means 23 comprises a fitting 24 adapted to releasably engage a disposable tube, for example a needle 25.

The fluid regulation means 21 may be adapted to hold the disposable needle 25 substantially parallel with longitudinal axis L-L of the elongate member 22.

The elongate member 22 is mounted to a mounting aperture 26 in the body 1 of the apparatus.

In a preferred embodiment both the elongate member 22 and the mounting aperture 26 are substantially circular in transverse cross section. The elongate member 22 is preferably provided with O-ring seals 27 to seal against the mounting aperture 26.

The mounting aperture 26 is in fluid communication with an outlet aperture 28 provided in the body 1.

In use, a needle 25 is mounted to the fitting 24. The vertical position of the fluid regulation means 21 relative to the body 1 is adjusted by sliding the elongate member 22 up or down in the mounting aperture 26 as required. The position is adjusted until the tip 29 of the needle 25 is at the level required of the fluid in the well 4.

The fluid level regulation means 21 is preferably held in position by the friction between the O-ring seals 27 and the mounting aperture 26, but suitable locking means (not shown) may additionally or alternatively be used.

When a vacuum is applied to the outlet aperture 28, fluid is drawn out of the upwardly open port 17 by the needle 25. The rate at which the fluid can be removed from the well 4 by the vacuum exceeds the rate at which the fluid is supplied though the inlet means 10. In this way the level of fluid in the well 4 is maintained at the level of the tip 29 of the needle 25.

Referring back to FIG. 2, the chamber assembly 2 is also provided with an outer moat portion 15A. The outer moat portion 15A may be used to accumulate the perfusion fluid when a vacuum source is not available. The fluid may be transferred from the inner moat 15 to the outer moat 15A by the use of suitable wicking material (not shown). The outer moat portion 15A may be provided with a drain aperture (not shown) to allow it to drain.

Figure 5:
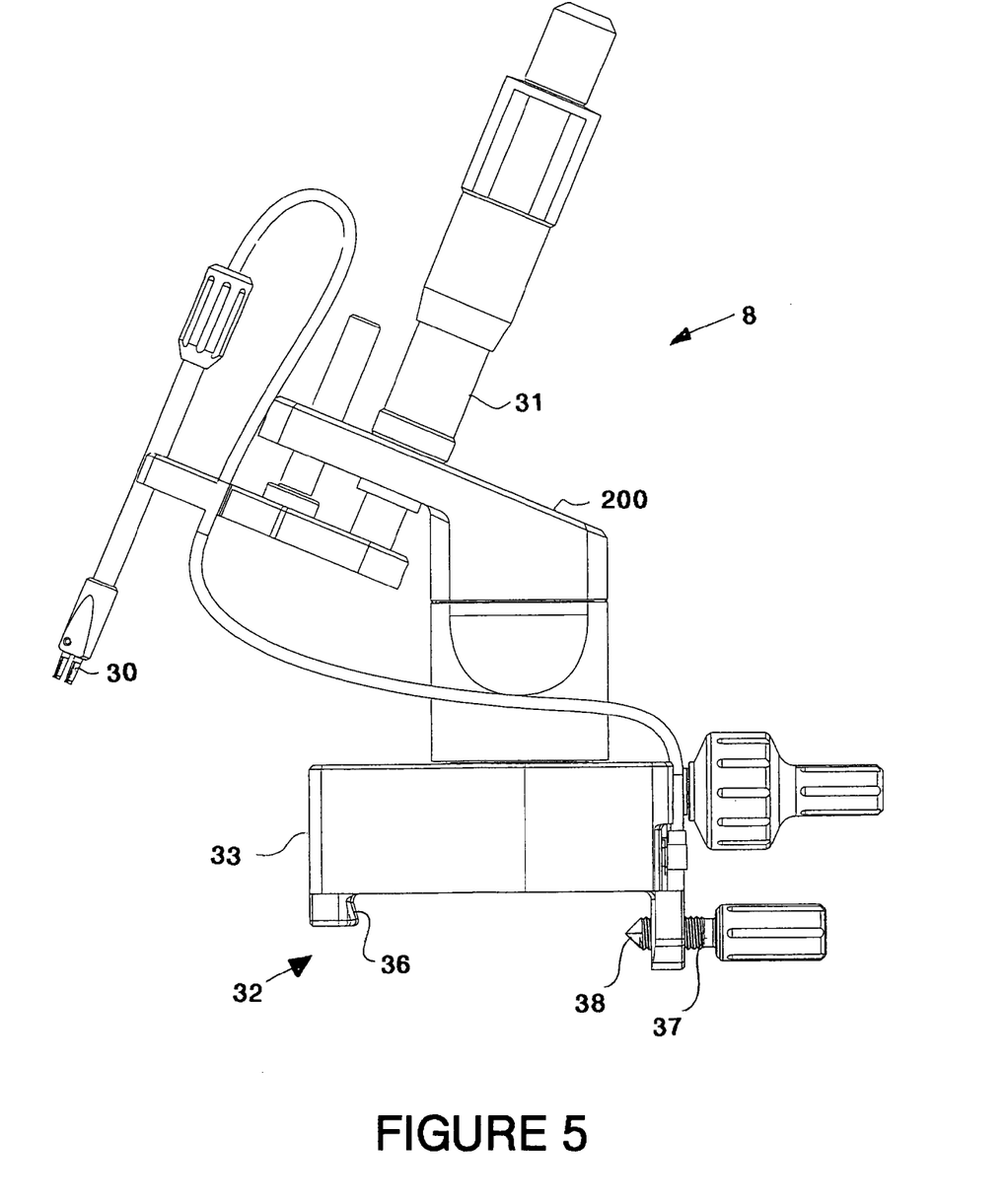
FIG. 5: Shows a side view of the stimulating means of the apparatus of FIG. 1.

Referring next to FIGS. 1 and 5, the stimulating and detecting means 8,9 preferably comprise an electrode 30 engaged with a mounting means, generally referenced by arrow 200. The mounting means comprises a micromanipulator mechanism 31.

The mounting means 200 comprises gripping means 32 adapted to engage the body 1. The body 1 is shaped so that gripping means 32 provided at the base 33 of the mounting means 200 can engage with an inner surface 34 (best seen in FIG. 2) of the electrically conductive annular member 19, and with an outer surface 35 of the base 3. The gripping means 32 comprises an electrically conductive gripping member 36 which engages with the inner surface 34 of the electrically conductive annular member 19. The electrically conductive gripping member 36 is connected to a suitable terminal to allow electrical connection to the data recording system.

In a preferred embodiment the electrically conductive annular member 19 is coaxial with the disc shaped base 3. The electrically conductive gripping member 36 of the gripping means 32 is a flange, and the outer part of the gripping means 32 is a screw 37 which can be tightened onto the outer surface 35 of the base 3. In a preferred embodiment the screw 37 has a pointed head 38, and the outer surface 35 of the base is provided with a circumferential groove 39 into which the pointed head seats. In this way, the stimulating and detecting means 8, 9 can be moved to any radial position on the base 3, while maintaining the contact to the common earth 19. The quality of the contact between the conductive gripping member 36 and the earth 19 is increased as the gripping or clamping force is increased.

As shown in FIG. 2, the net assembly 6 sits snugly inside the cradle formation 5. An O-ring (not shown) may be provided to create a seal between the outside of the net assembly 6 and the tapering wall 7A of the cradle formation 5.

Figure 6:
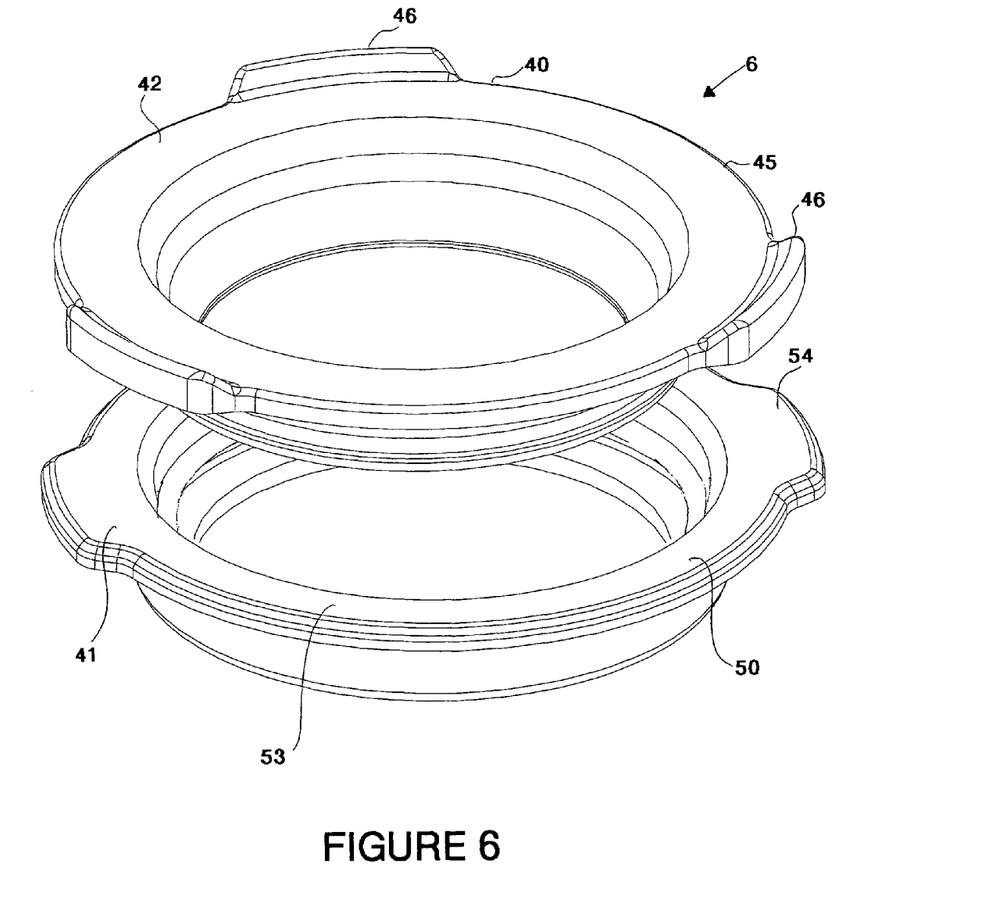
FIG. 6: Shows an exploded perspective view of a net assembly of the apparatus of FIG. 1.
Figure 7:
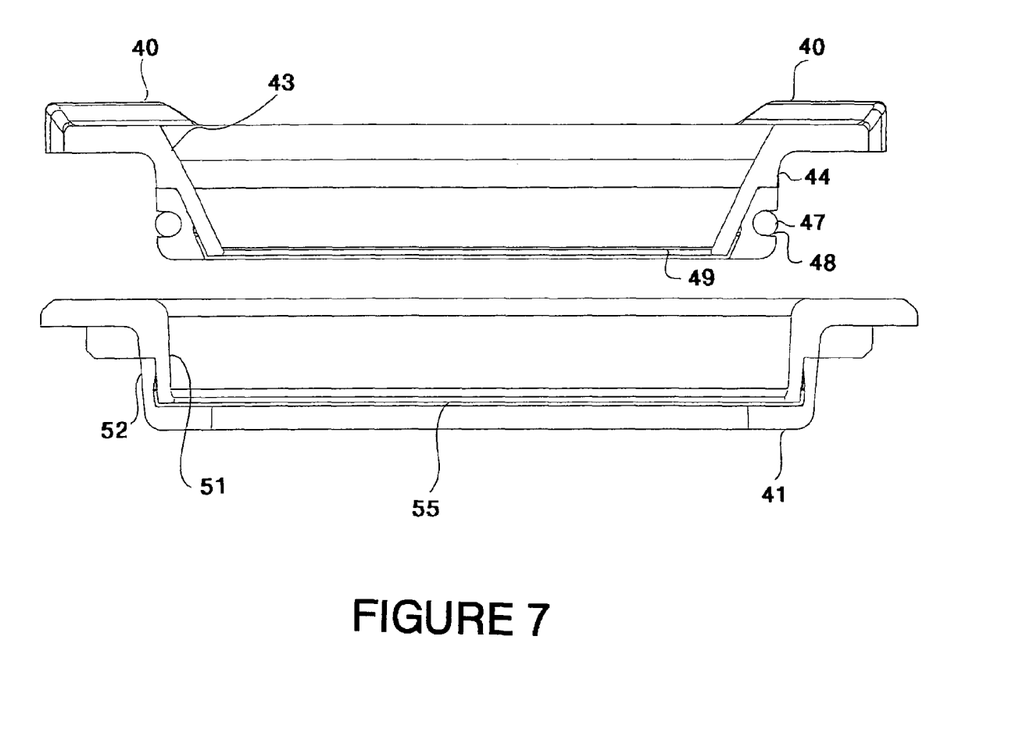
FIG. 7: Shows an exploded cross-section of the net assembly of FIG. 6.

Referring next to FIGS. 6 and 7, the net assembly 6 comprises a first net means 40 which is nestable inside a second net means 41.

The first net means 40 comprises a substantially annular frame 42 with a substantially frusto-conical inner surface 43 and a substantially cylindrical outer surface 44. A flange 45 is provided around the upper circumference of the first net, the flange 45 provided with a plurality of tab formations 46 protruding radially outward. An O-ring seal 47 is engaged with a suitable groove 48 in the outer surface 44 of the first net, and provides a suitable friction force between the first and second nets 40, 41 when they are engaged. Suitable netting material 49 is provided at the opposite end of the frame from the flange 45.

The second net means 41 is provided with a substantially annular frame 50 which has substantially cylindrical inner and outer surfaces 51, 52, and is also provided with a flange 53 having tab formations 54 which protrude radially outward. In a preferred embodiment the tab formations of both nets 40, 41 are spaced evenly apart. It is preferred that the first net 40 has a different number of tabs 46 from the number of tabs 54 on the second net 41, in order to avoid the tabs 46, 54 from aligning, which would make separation of the nets 40, 41 more difficult. The second net 41 is also provided with suitable netting material 55 at the opposite end of the frame to the flange 53. Types of suitable netting material for the first and second nets will be known to those skilled in the art.

In some embodiments a second O-ring (not shown) may be provided around the exterior of the second net means 41, in order to grip the inner walls of the cradle formation 5.

Those skilled in the art will appreciate that the frusto-conical shape of the inner surface 43 of the first net 40 reduces or substantially eliminates the "dead" area of the first net 40, that is, the area which is inaccessable by the stimulating and recording means 8, 9.

The nets 40, 41 are preferably manufactured by an injection moulding process.

Figure 8:
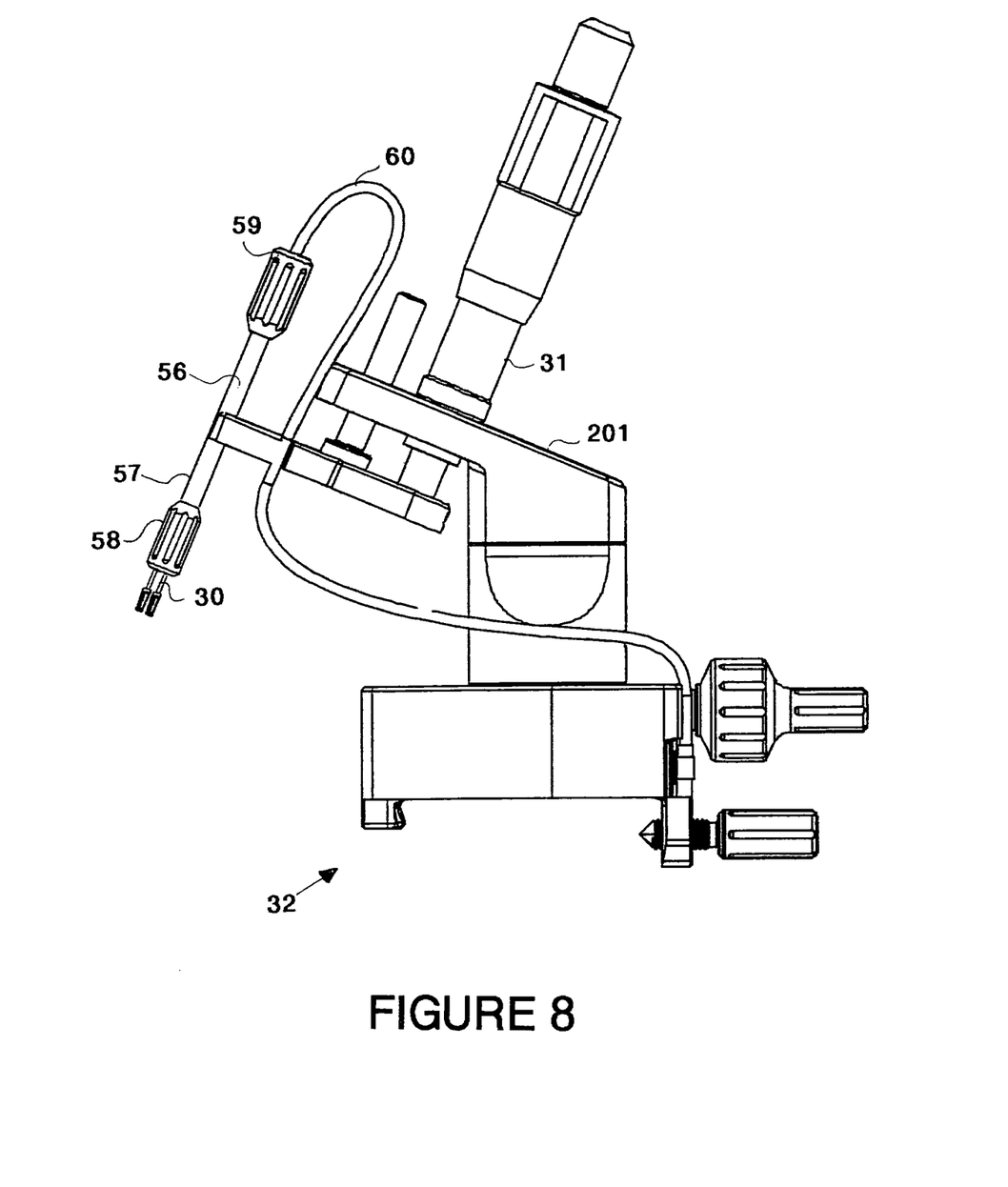
FIG. 8: Shows a side view of the stimulating means with an alternative electrode mounting means.

Referring next to FIG. 8, a stimulating means 8 is shown with an alternative electrode mounting means, generally referenced 201, to that shown in FIG. 5.

In the embodiment shown in FIG. 8 the electrode mounting means 201 comprises a micromanipulator means 31 and gripping means 32 which are the same as those provided in the embodiment shown in FIG. 5. However, the electrode mounting means 201 is provided with an electrode engaging means 56 which comprises a sheath 57. The sheath 57 is preferably formed from a hollow tube, typically made from steel or the like.

A first end of the sheath 57 is provided with a chuck 58. The chuck 58 is preferably of the collet chuck type, although other chucks may be suitable. The collet is preferably integral with the sheath 57.

The chuck 58 is adapted to releasably grip the electrode 30 in an "in use" position, as shown in FIG. 8.

The sheath 57 is shaped and dimensioned to allow the electrode 30 to be retracted inside the sheath 57 when not in use. In this way the electrode 30 can be protected when the apparatus 100 is not in use and/or when the electrode mounting means 201 is being engaged or disengaged from the apparatus 100.

The distal end of the sheath 57 is preferably also provided with a second chuck 59 which can engage the cable 60 which carries the signal to or from the electrode 30. The second chuck 60 is preferably also of the collet chuck type. The electrode mounting means 201 may also be used with the detecting means.

Those skilled in the art will appreciate that the present invention provides an apparatus for testing electrical activity from a biological tissue sample which is relatively simple and portable, but which may be more reliable than comparable apparatus of the prior art.

Unless the context clearly requires otherwise, throughout the description and the claims, the words "comprise", "comprising", and the like, are to be construed in an inclusive sense as opposed to an exclusive or exhaustive sense, that is to say, in the sense of "including, but not limited to".

Where in the foregoing description, reference has been made to specific components or integers of the invention having known equivalents, then such equivalents are herein incorporated as if individually set forth.

Although this invention has been described by way of example and with reference to possible embodiments thereof, it is to be understood that modifications or improvements may be made thereto without departing from the spirit or scope of the appended claims.

The invention claimed is:

1. An apparatus for testing electrical activity from a biological tissue sample, the apparatus comprising a body provided with a well, the apparatus further comprising stimulating means for stimulating a biological tissue sample which is located, in use, in the well, and detecting means for detecting electrical activity in the tissue sample, the apparatus further comprising a fluid inlet means in fluid communication with the well and a fluid outlet means in fluid communication with the well, wherein the inlet means comprises an electrically conductive conduit and the outlet means comprises an outlet passage provided in the body, and wherein the electrically conductive conduit of the fluid inlet means extends through a portion of the outlet passage and is in fluid contact with a fluid flowing, in use, through the outlet passage.

2. The apparatus of claim 1 wherein the body is provided with an electrically conductive member which is electrically connectable to the electrically conductive conduit.

3. The apparatus of claim 1 wherein the electrically conductive conduit has an electrical resistivity of less than $1 \times 10^{-6}$ Ωm at room temperature.

4. The apparatus of claim 1 wherein the electrically conductive conduit has a thermal conductivity of at least 10 W/m K at room temperature.

5. The apparatus of claim 4 wherein the fluid outlet means comprises a passage adapted to receive a heating element such that the heating element is in thermal contact with fluid flowing though the outlet conduit upstream of the electrically conductive conduit, to thereby transfer heat to the fluid in the inlet means through the electrically conductive conduit.

6. An apparatus for testing electrical activity from a biological tissue sample, the apparatus comprising a body provided with a well, stimulating means for stimulating a biological tissue sample located, in use, in the well, and detecting means for detecting electrical activity in the tissue sample, a fluid inlet means in fluid communication with the well and a fluid outlet means in fluid communication with the well, wherein the fluid inlet means comprises an electrically conductive conduit and the fluid outlet means comprises an outlet passage provided in the body wherein the electrically conductive conduit of the fluid inlet means extends through a portion of the outlet passage and is in fluid contact with a fluid flowing, in use, through the outlet passage, the apparatus further comprising an electrically conductive member in electrical contact with the fluid contained, in use, in at least one of the well, the inlet means and the outlet means, wherein at least one of the stimulating means and detecting means is engaged with the body by a gripping means which comprises an electrically conductive gripping member which engages the electrically conductive member, and the electrically conductive gripping member is electrically connectable to a data recording system which, in use, records the electrical activity from the sample.

7. The apparatus of claim 6 wherein the electrically conductive member comprises an annular ring.

8. The apparatus of claim 7 wherein the annular ring is set into the body.

9. The apparatus of claim 7 wherein the electrically conductive gripping member exerts a force on an inner surface of the annular ring in a radially outward direction.

10. An apparatus for testing electrical activity from a biological tissue sample, the apparatus comprising a body provided with a well, the apparatus further comprising stimulating means for stimulating a biological tissue sample which is located, in use, in the well, and detecting means for detecting electrical activity in the tissue sample, the body provided with a fluid inlet means in fluid communication with the well and outlet means comprising an upwardly open outlet port in fluid communication with the well, and adjustable fluid level regulation means adapted to draw fluid, in use, from the upwardly open outlet port at a required level, the outlet means comprising an outlet passage provided in the body and an outlet aperture which is substantially fixed in position relative to the body, and further wherein the fluid inlet means comprises an electrically conductive conduit which extends through a portion of the outlet passage and is in fluid contact with a fluid flowing, in use, through the outlet passage.

* * * * *